United States Patent
Israel-Assayag et al.

(10) Patent No.: US 9,944,610 B2
(45) Date of Patent: Apr. 17, 2018

(54) PREPARATION AND METHOD FOR USE IN THE TREATMENT OF RESPIRATORY DISEASES

(71) Applicant: Universite Laval, Quebec, Quebec (CA)

(72) Inventors: Evelyne Israel-Assayag, Sainte-Foy (CA); Pierre Lavallee, Rosemere (CA); Yvon Cormier, Neuville (CA); Bildad Nyambura, Reading (GB)

(73) Assignee: UNIVERSITÉ LAVAL, Québec (CA)

( * ) Notice: Subject to any disclaimer, the term of this patent is extended or adjusted under 35 U.S.C. 154(b) by 0 days.

(21) Appl. No.: 14/776,483

(22) PCT Filed: Mar. 12, 2014

(86) PCT No.: PCT/CA2014/050218
§ 371 (c)(1),
(2) Date: Sep. 14, 2015

(87) PCT Pub. No.: WO2014/138975
PCT Pub. Date: Sep. 18, 2014

(65) Prior Publication Data
US 2016/0046587 A1    Feb. 18, 2016

Related U.S. Application Data

(60) Provisional application No. 61/778,845, filed on Mar. 13, 2013.

(51) Int. Cl.
*C07D 243/08* (2006.01)
*A61K 31/551* (2006.01)
*C07C 211/53* (2006.01)
*A61K 9/00* (2006.01)

(52) U.S. Cl.
CPC .......... *C07D 243/08* (2013.01); *A61K 9/0075* (2013.01); *A61K 31/551* (2013.01); *C07C 211/53* (2013.01); *C07B 2200/13* (2013.01)

(58) Field of Classification Search
CPC ................................................... C07D 243/08
See application file for complete search history.

(56) References Cited

U.S. PATENT DOCUMENTS 8,557,804 B2 * 10/2013 Cormier ............... C07D 243/08
514/183

FOREIGN PATENT DOCUMENTS

WO    2006/005195 A1    1/2006

OTHER PUBLICATIONS

Mastalerz H. et al., "Novel C-5 aminomethyl pyrrolotriazine dual inhibitors of EGFR and HER2 protein tyrosine kinases" Elsevier, ScienceDirect, Bioorganic & Medicinal Chemistry Letters, vol. 17, No. 10, pp. 2828-2833, 2007, XP_22049596A.
Song D. et al., "Design, synthesis and biological evaluation of novel aliphatic amido/sulfonamido-quaternary ammonium salts as antitumor agents" Elsevier, Bioorganic & Medicinal Chemistry, vol. 21, No. 3, pp. 788-794, 2013, XP_28975837A.
Toma L. et al., "6-Chloropyridazin-3-yl Derivatives Active as Nicotinic Agents: Synthesis, Binding, and Modeling Studies" J. Med. Chem., vol. 45, No. 18, pp. 4011-4017, 2002, XP-002356220.
Extended European Search Report (Communication) dated Jul. 26, 2016, issued by the European Patent Office in corresponding European Application No. EP 14765759.7-1452 (7 pages).
Office Action (Communication pursuant to Rules 70(2) and 70a(2) EPC) dated Aug. 12, 2016, by the European Patent Office in corresponding European Application No. 14765759.7-1452, (1 page).
Zisman et al., "Cyclophosphamide in the Treatment of Idiopathic Pulmonary Fibrosis: A Prospective Study in Patients who Failed to Respond to Corticosteroids", Chest, Jun. 2000, vol. 117, No. 6, pp. 1619-1626.
International Search Report (Form PCT/ISA/210) dated May 28, 2014, by the Canadian Patent Office in corresponding International Application No. PCT/CA2014/050218. (4 pages).

* cited by examiner

*Primary Examiner* — Kahsay Habte
(74) *Attorney, Agent, or Firm* — Buchanan Ingersoll & Rooney P.C.

(57) ABSTRACT

The present disclosure relates to a novel active compound having the formula Ia:

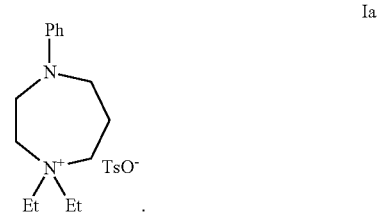

Figure 1:
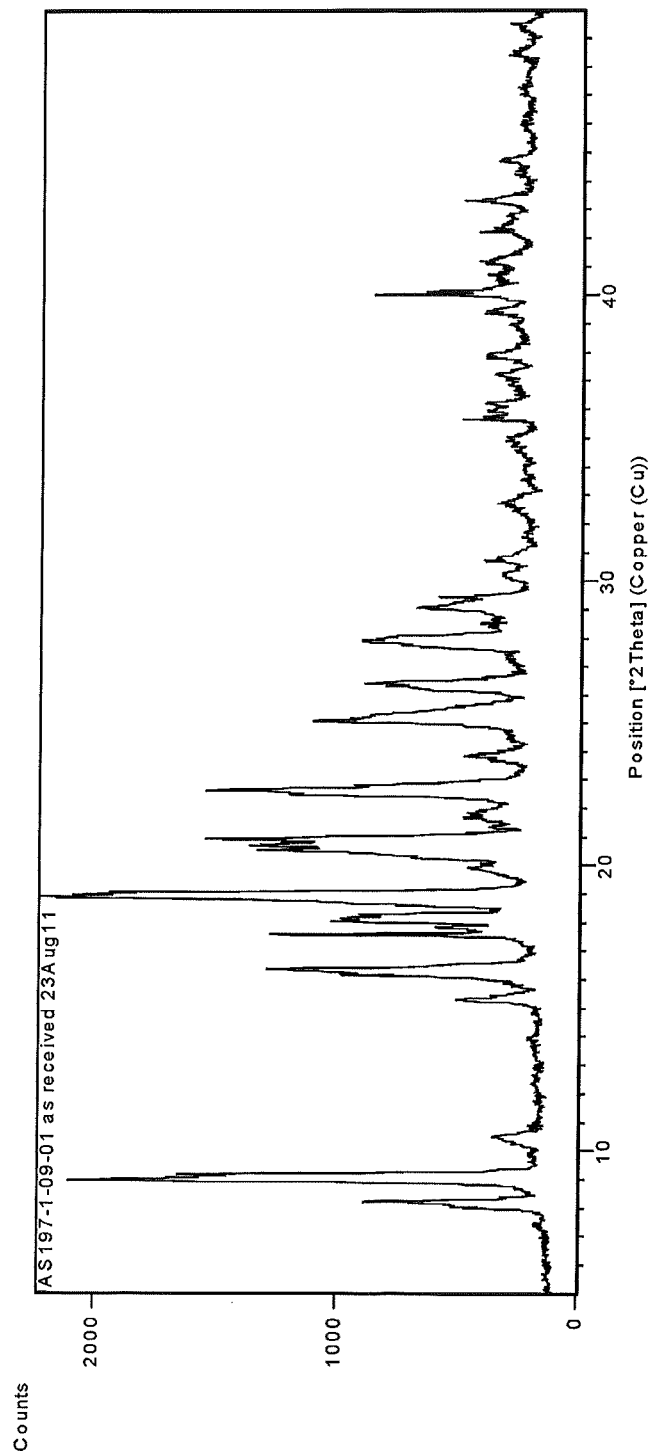

solid preparations, uses and methods for the treatment or prevention of respiratory diseases comprising said compound as well as process of preparation thereof.

9 Claims, 4 Drawing Sheets

PREPARATION AND METHOD FOR USE IN THE TREATMENT OF RESPIRATORY DISEASES

FIELD OF THE DISCLOSURE

The present disclosure relates to a novel active compound, solid preparations, uses and methods for the treatment or prevention of respiratory diseases as well as process of preparation thereof.

BACKGROUND OF THE DISCLOSURE

Asthma is an inflammatory disease of the airways that affects millions of people globally. Recent studies have shown that asthma remains inadequately controlled in many patients, despite treatment in accordance with guidelines. There is clearly an unmet need for the effective and safe treatment of patients with asthma who remain symptomatic despite optimized standard treatment. A strong association exists between asthma control/hospitalization and asthma-related mortality. While all patients are susceptible to exacerbations, uncontrolled asthma increases the risk of an exacerbation being life-threatening or fatal.

Chronic obstructive pulmonary disease (COPD) is common world-wide. The prevalence of the disease continues to grow in most industrialized nations. It is mostly associated with cigarette smoking. Although COPD is a leading cause of illness and death, its recognition as a public health problem has been slow to evolve despite the rising mortality rate for COPD. Additionally, COPD imparts substantial economic burden on individuals and society.

The treatment of interstitial lung disease such as interstitial pulmonary fibrosis (IPF), Sarcoidosis, hypersensitivity pneumonitis (HP), and bronchiolitis obliterans with organizing pneumonitis (BOOP) basically rests on the use of systemic corticosteroids. This treatment is effective in controlling some of the inflammation but induces serious side effects and does not reverse underlying fibrotic changes. Immunosupressive agents such as cyclophosphamide and azathioprine are sometimes tried in severe IPF but their therapeutic values are unproven and at most, very limited (Zisman D et al. Cyclophosphamide in the treatment of idiopathic pulmonary fibrosis: a prospective study in 45 patients who failed to respond to corticosteroids. Chest 2000, 117: 1619-1626). In essence, lung fibrosis is usually progressive and untreatable, with most IPF patients dying of this condition. The above suggest there is still a need for a therapy that offers benefit to current treatments of respiratory diseases such as asthma and COPD. Inhalation drug delivery has been an attractive approach for drug administration and treatment of pulmonary diseases since inhaled drugs are localized to the target organ, which generally allows for a lower dose than is necessary with systemic delivery.

Various techniques and devices may be used to deliver a drug to the lung such as metered-dose inhaler (MDI), dry powder inhaler (DPI) and nebulizer. Each technique and device has advantages, challenges and limitations. For example, MDIs which contained chlorofluorocarbons (CFC) to deliver the drug and many of these have been phased out over the recent years. Nebulization may be suitable in a hospital setting however the administration of a drug requires particular physico-chemical properties of the active agent and may involve substantial patient and professional time and as such reduce patient compliance.

DPI preparations have to overcome various difficulties for effective drug delivery. For example, the small size of the inhalable particles subjects them to forces of agglomeration and cohesion, resulting in poor flow performance and non-uniform dispersion. Pharmaceutical preparations for DPI therefore often require that the active ingredient be blended with a carrier to improve flow properties. The efficiency of a DPI powder is therefore often dependent on the carrier characteristics. Although the manufacture of a suitable drug product and the effective performance of DPI products are dependent on the inhaler device, drug deposition in the lung is also dependant on many factors including the size, and the aerodynamics the physicochemical properties of the active ingredient particles.

In addition, various agents are now used with the active ingredient and/or the carrier or excipient to modify the "performance" of the DPI preparations to improve flow, reduce inter-particulate adhesion and reduce moisture effects, and thereby achieve improved particle deposition in lungs. For example, the addition of magnesium stearate to inhalation powders is reported to improve aerosol performance and increase moisture resistance.

Furthermore, it is often desirable to control the moisture content in the active pharmaceutical ingredient (API), and optionally the carriers, excipients, packaging materials (primary and secondary), and the manufacturing environment. Moisture sensitivity may require special manufacturing processes/treatments for packaging materials, especially for those in direct content with the pharmaceutical preparation.

SUMMARY

In one aspect, there is provided a crystalline form of the compound having the formula Ia:

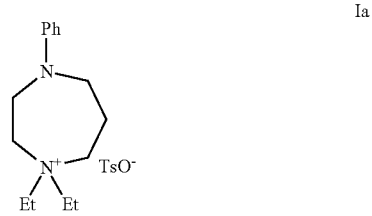

In one aspect, there is provided a micronized crystalline form of the compound having the formula Ia.

In one aspect, there is provided a process for producing particles of the compound of formula Ia of a size less than about 10 microns, comprising micronizing the compound having particles of a size greater than about 10 microns.

In one aspect, there is provided a method for treating or preventing respiratory diseases comprising administering an effective amount of an inhalable micronized compound having the formula Ia.

In one aspect, there is provided a method for treating or preventing pulmonary inflammation, inducing airway smooth muscle relaxation and improving airway hyperresponsiveness in an asthma or COPD patient which comprises administering effective amount of an inhalable micronized compound having the formula Ia.

In one aspect, there is provided a pharmaceutical preparation comprising an effective amount of an inhalable micronized compound having the formula Ia.

In one aspect, there is provided a drug product consisting of a capsule suitable for use with a DPI, said capsule comprising an effective amount of an inhalable micronized compound having the formula Ia.

In one aspect, there is provided a process for preparing a compound of formula I or Ia as defined herein.

In one aspect, there is provided a kit for use in the treatment or prevention of respiratory diseases in a patient in need thereof, the kit comprising a capsule or capsules suitable for use with a DPI, said capsule comprising an effective amount of an inhalable micronized compound of formula Ia and instructions for treating or preventing respiratory diseases of a patient in need thereof.

BRIEF DESCRIPTION OF THE FIGURES

FIG. 1 shows a XRPD diffractogram of the active ingredient;

FIG. 2 shows a particle size distribution graph of the micronized active ingredient;

FIG. 3 shows the fine particles mass (FPM) results of NGI testing;

FIG. 4 shows an overlay of XRPD diffractograms of the active ingredient after crystallization and after micronization.

DETAILED DISCLOSURE

Micronization:

The disclosure relates to powders for inhalation consisting of micronized active substance. The term “for inhalation” or “inhalable” means those particles which are transported deep into the branches of the lungs when inhaled with the inspired air. It is generally accepted that the particle size required for this is less than about 10 microns, preferably less than 6 microns and preferably between about 1 microns to 5 microns.

Various milling techniques are known. For example, jet milling can be used to reduce the particle size of compounds to produce particles smaller than 10 micron for inhalation administration. Other techniques such as High Pressure Homogenizer (HPH) and Spray Drying (SD), supercritical solvent, spray drying, spray freezing, and controlled precipitation may also be used to the extent that they can produce the required particle size and distribution without causing a detrimental effect to the active agent. In the examples below, particles were micronized using jet milling.

Micronization can reproducibly deliver product within the size range required for the development of inhalation products. As discussed above, particles are required to be less than about 10 microns, in order to be inhaled into the respiratory tract and down to the lungs. Particles greater in size than this will impact on the back of the throat where there is limited therapeutic benefit. Equally, if there are too many ‘fines’ present in the micronized product, once formulated, these again offer little therapeutic value, as they are often exhaled with the patient’s next breath. The method by which the micronized drug product is produced can normally be chosen and adapted to generate an acceptable particle size distribution.

Dry Powder Inhaler (DPI):

DPIs can be complex devices and their performance depends on several aspects such as the design of the inhaler, the powder preparation used and the air flow generated by the patient through the inhaler. The DPI may be a pre-weighed dose or multi-dose reservoir. The pre-weighed system may perform the delivery through capsules or blisters containing pre-weighed unit doses that are inserted into the device during manufacture or by the patient before use. Thereafter, the dose may be inhaled directly from the pre-metered unit or it may be transferred to a chamber before being inhaled by the patient. Multi-dose reservoir systems provide the desired unit dose by volumetric measurement of powder through the action of gravity. In general, to be suitable, multi-dose systems require certain properties of the powder. Although pre-weighed dose systems are preferred for use in this disclosure, it is contemplated that multi-dose system may be used as well.

DPIs may also be classified according to the air flow resistance of the device and labels such as high resistance, low resistance or standard resistance are sometimes assigned to the device although the labelling may be relative. The air flow resistance of some marketed DPI ranges from 0.015 to about 0.5 ($kPa^{0.5}L^{-1}$ min). Regardless of the DPI design, crucial attributes include the reproducibility of the dose and particle size distribution. The skilled practitioner can determine which DPI may be used with the active ingredient.

Capsules and Blisters in DPI

Dry-powder formulations using single-dose capsule inhaler allows for high fill weight up to 40 mg thus allowing delivery of high doses of medication. Various types of capsules or blisters can be used in DPIs. Examples of capsules include gelatin, gelatin/PEG and Hydroxy propyl methyl cellulose (HPMC) hard capsules. The choice of the appropriate capsule may be determined by the skilled practitioner and will depend on factors including the physico-chemical properties of the active ingredient, the capsule size to accommodate the actual dose of medication, the device used as well as the storage time and conditions. For example, the capsule material should not be too brittle to produce detached particles and it should not be so elastic that it returns and recloses the hole before the active agent is withdrawn from the capsule. Also, the moisture content of the capsule material will be a relevant consideration in particular if moisture can affect the stability, flow properties, potential to aggregate and homogeneity of the micronized agent. The mechanical properties (e.g. puncturing force required and holes morphology) will also be considered.

Respiratory Diseases

In one embodiment, the disease as defined herein is selected from the group consisting of asthma, chronic obstructive pulmonary disease (COPD), interstitial pulmonary fibrosis (IPF), sarcoidosis, hypersensitivity pneumonitis (HP) and bronchiolitis obliterans with organizing pneumonitis (BOOP).

In one embodiment, the disease is asthma and COPD. In one embodiment, the disease is asthma. In one embodiment, the disease is COPD. In one embodiment, the disease is IPF. In one embodiment, the disease is sarcoidosis. In one embodiment, the disease is HP. In one embodiment, the disease is BOOP.

In one embodiment, the diseases comprise one or more of asthma, including bronchial, allergic, intrinsic, extrinsic, exercise-induced, drug-induced (including aspirin and NSAID-induced) and occupational asthma, both intermittent and persistent and of all severities, and other causes of airway hyper-responsiveness; chronic obstructive pulmonary disease (COPD); bronchitis, including infectious and eosinophilic bronchitis; emphysema; bronchiectasis; cystic fibrosis; sarcoidosis; hypersensitivity pneumonitis; lung fibrosis, including cryptogenic fibrosing alveolitis, idiopathic interstitial pneumonias, fibrosis complicating anti-neoplastic therapy.

Without being bound to theory, it is believed that the homopiperazine compound of the invention exerts a dual nicotinic and muscarinic activity. In addition, ASM-024 mechanism of action appears to involve a direct action on airway smooth muscle cells (SMC) by a mechanism independent of cGMP or cAMP pathways. Moreover, ASM-024 had no relaxant effect on LTD4-induced contraction suggesting a mechanism of action independent from the leukotriene pathway.

As used herein, "treatment" or "treating" at least refers to controlling or ameliorating at least one disease described herein or associated symptoms, at least for the duration of said treatment.

Although not limited to such patients, "prevention" or "prophylaxis" treatment (which may be used interchangeably) is expected to be particularly useful to the treatment of patients who have suffered a previous episode associated with diseases described herein, or are otherwise considered to be at increased risk of said diseases. A successful preventive treatment would normally be expected to i) reduce the occurrences of a further episode, ii) reduce its severity or iii) prevent occurrences of further episodes, at least for the duration of the therapy.

It will also be appreciated that the amounts of therapeutic agent for use in treatment will vary with the nature of the condition for which treatment is required as well as the age and condition of the patient and will be ultimately at the discretion of the physician.

Pharmaceutical Preparation and Drug Product

In one embodiment, there is provided a pharmaceutical preparation comprising an effective amount of an inhalable micronized compound having the formula Ia.

In one embodiment, there is provided a pharmaceutical preparation comprising an effective amount of an inhalable micronized compound having the formula Ia and a carrier suitable for use in an inhalable dry powder.

In one embodiment, there is provided a pharmaceutical preparation comprising an effective amount of an inhalable micronized compound having the formula Ia, a carrier suitable for use in an inhalable dry powder and one or more agent to modify the performance such as magnesium stearate.

In one embodiment, there is provided a pharmaceutical preparation comprising an effective amount of an inhalable micronized compound having the formula Ia, and one or more agent to modify the performance such as magnesium stearate.

In one embodiment, there is provided a pharmaceutical preparation consisting of an effective amount of an inhalable micronized compound having the formula Ia.

In one embodiment, there is provided a pharmaceutical preparation consisting of an effective amount of an inhalable micronized compound having the formula Ia and one or more agent to modify the performance such as magnesium stearate.

In one embodiment, there is provided a pharmaceutical preparation consisting of an effective amount of an inhalable micronized compound having the formula Ia and a carrier suitable for use in an inhalable dry powder.

In one embodiment, there is provided a pharmaceutical preparation consisting of an effective amount of an inhalable micronized compound having the formula Ia, a carrier suitable for use in an inhalable dry powder and one or more agent to modify the performance such as magnesium stearate.

In one embodiment, there is provided a drug product consisting of a capsule suitable for use with a DPI, said capsule comprising an effective amount of an inhalable micronized compound having the formula Ia.

In one embodiment, there is provided a drug product consisting of a capsule suitable for use with a DPI, said capsule comprising an effective amount of an inhalable micronized compound having the formula Ia and a carrier suitable for use in an inhalable dry powder.

In one embodiment, there is provided a drug product consisting of a capsule suitable for use with a DPI, said capsule comprising an effective amount of an inhalable micronized compound having the formula Ia, and one or more agent to modify the performance such as magnesium stearate.

In one embodiment, there is provided a drug product consisting of a capsule suitable for use with a DPI, said capsule comprising an effective amount of an inhalable micronized compound having the formula Ia, a carrier suitable for use in an inhalable dry powder and one or more agent to modify the performance such as magnesium stearate.

In one embodiment, there is provided a drug product consisting of a capsule suitable for use with a DPI, said capsule consisting of an effective amount of an inhalable micronized compound having the formula Ia.

In one embodiment, there is provided a drug product consisting of a capsule suitable for use with a DPI, said capsule consisting of an effective amount of an inhalable micronized compound having the formula Ia and an carrier suitable for use in an inhalable dry powder.

In one embodiment, there is provided a drug product consisting of a capsule suitable for use with a DPI, said capsule consisting of an effective amount of an inhalable micronized compound having the formula Ia, and one or more agent to modify the performance such as magnesium stearate.

In one embodiment, there is provided a drug product consisting of a capsule suitable for use with a DPI, said capsule consisting of an effective amount of an inhalable micronized compound having the formula Ia, a carrier suitable for use in an inhalable dry powder and one or more agent to modify the performance such as magnesium stearate.

In one embodiment, there is provided a kit for use in the treatment or prevention of respiratory diseases in a patient in need thereof, the kit comprising a capsule or capsules or blisters suitable for use with a DPI, said capsule or blister comprising an effective amount of an inhalable micronized compound of formula Ia and instructions for treating or preventing respiratory diseases of a patient in need thereof. Optionally the kit may further comprise one or more packaging material for said capsule or blister. Optionally the kit may further comprise a desiccant in the primary and/or secondary packaging to maintain a desirably low relative humidity.

Synthesis and Chemical Intermediates

Scheme 1 is one possible general process for synthesizing ASM-024

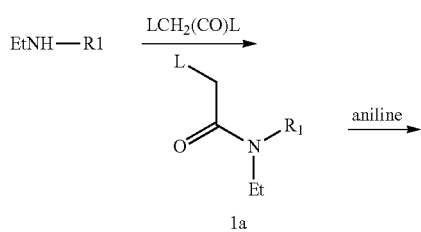

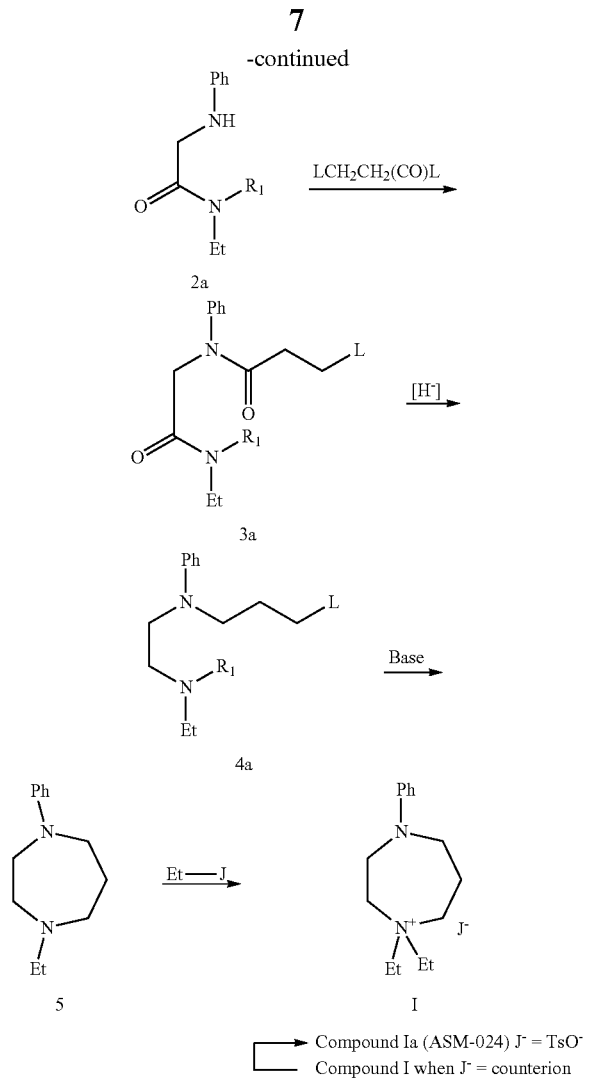

The process can be described as follows in general terms. An ethylamine of formula EtNH—R1 is reacted with a reagent of formula LCH$_2$(CO)L (optionally in the presence of an organic solvent, preferably a haloalkyl solvent such as dichloromethane) to provide the amide 1a wherein R1 is H or a suitable protective group and L is the same or different and is a leaving group. Preferably, R1 is H; preferably L is a halide and more preferably a chloride. The leaving group L on compound 1a is reacted with aniline (optionally in the presence of an organic solvent, preferably a polar organic solvent such as an alcohol and optionally with heating) to provide compound 2a. The reagent of formula LCH$_2$CH$_2$(CO)L is reacted with compound 2a (optionally in the presence of an organic solvent, preferably a polar organic solvent such as a acetone) to provide compound 3a, wherein L is as defined previously, which is treated with a suitable reducing agent, preferably a hydride donor such as a boron hydride (in the presence of an organic solvent and optionally with heating), to provide compound 4a. If R1 is a protective group, it can be removed at any stage before the cyclization reaction.

The expression "protective group" includes any suitable protecting groups for protecting the amino moiety. Examples of protecting groups can be found in Green et al., "Protective Groups in Organic Chemistry", (Wiley, 4th ed. 2007) and Harrison et al. "Compendium of Synthetic Organic Methods" (John Wiley and Sons, 1996).

Compound 4a is cyclized in presence of a base (preferably an inorganic base such as a carbonate) and optionally in the presence of a reagent for facilitating the functional role of the leaving group L such as NaBr, KBr, KI) to provide compound 5a. Compounds 4a and 5 may also be formed/transformed into a synthetically suitable salt for the purpose of isolation or purification.

In the context of this disclosure, a "synthetically suitable salt" is a salt that may or may not be a pharmaceutically acceptable salt and that is used in one or more steps of a process to obtain a desired intermediate.

Compound 5 is in turn reacted with a suitable reagent for introducing an ethyl group on the non-aromatic tertiary amine and produce the quaternary ammonium functionality wherein J$^-$ is a counterion. When J$^-$ is tosylate (TsO$^-$) compound ASM-024 is obtained without further modification, otherwise when J$^-$ is other than tosylate, the resulting counterion can be exchanged for a tosylate using ion exchanged method known in the art. Compound I (or Ia) can optionally be purified using techniques known in the art such as crystallization or chromatography.

In one embodiment, there is provided a process for preparing a compound of formula I and Ia wherein J- is TsO-comprising the steps as defined in scheme 1.

In one embodiment, there is provided a process for preparing a compound of formula I and Ia wherein J$^-$ is TsO$^-$ comprising conducting one or more steps defined in scheme 1 above, that is:

$$5 \longrightarrow \text{I or Ia}$$
$$4a \longrightarrow 5 \longrightarrow \text{I or Ia}$$
$$3a \longrightarrow 4a \longrightarrow 5 \longrightarrow \text{I or Ia}$$
$$2a \longrightarrow 3a \longrightarrow 4a \longrightarrow 5 \longrightarrow \text{I or Ia or}$$
$$1a \longrightarrow 2a \longrightarrow 3a \longrightarrow 4a \longrightarrow 5 \longrightarrow \text{I or Ia}$$

In one embodiment, there is provided a process for preparing a compound of formula I and Ia wherein J$^-$ is TsO$^-$ comprising the following steps:

In one embodiment, there is provided a process for preparing a compound of formula I and Ia wherein J⁻ is TsO⁻ comprising the following steps:

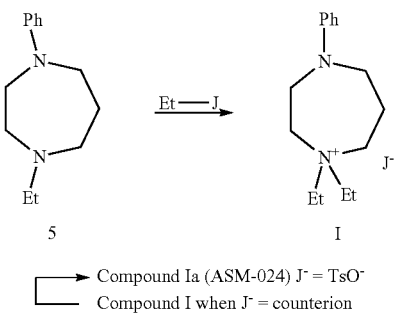

→ Compound Ia (ASM-024) J⁻ = TsO⁻
→ Compound I when J⁻ = counterion

In one embodiment, there is provided an intermediate of formula 4a

4a

Ph
|
N
 \
  \—L
  /
 N—R₁
 |
 Et or a synthetically suitable salt, wherein L is the same or different and is a leaving group. R1 is H or a suitable protective group. Preferably, R1 is H; preferably L is a halide and more preferably a chloride.

In one embodiment, there is provided an intermediate of formula 5

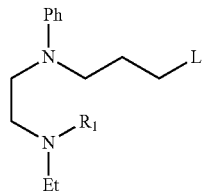

5 or a synthetically suitable salt.

In one embodiment, there is provided a crystalline compound of formula Ia

Ia

Ph
|
N
 \
  \
  /
 N⁺—TsO⁻
 / \
Et   Et

In one embodiment, the compound of formula Ia is anhydrate crystalline Form I.

In one embodiment, the compound of formula Ia is anhydrate crystalline Form I in an inhalable form.

In one embodiment, the compound of formula Ia is micronized inhalable anhydrate crystalline Form I.

The following examples are provided to further illustrate the aspects and embodiments of the present disclosure. They are not intended to be limitations on the scope of the instant invention in any way, and they should not be so construed. Furthermore, the compounds, methods and preparations, described in the following examples are not to be construed as forming the only genus that is considered as the invention.

General Rp-Hplc Conditions of the Synthetic Examples

HPLC analysis were performed on a Waters C18 reversed-phase analytical column (5 μm, Atlantis, 100×3.9 mm) using a flow rate of 1 mL/min and a gradient of 0% to 95% A/B over 15 min.

For the formation of ASM-024, the reaction was monitored using a Phenomenex CN reversed-phase analytical column (5 μm, Luna CN, 150×4.6 mm) with a flow rate of 0.5 mL/min and a gradient of 15% to 95% A/B over 20 min, where A=0.1% aqueous Formic Acid and B=CH3CN+0.1% FA Reagents: all reagents were obtained from Aldrich Co as "reagent" grade. Usual solvents and chemicals were obtained from VWR, A&C or Fisher and were also "reagent" grade. Commercial grade ethyl tosylate can be treated with triethyl amine to neutralize methyl tosylate that may be present as an impurity.

Example 1 Synthesis of ASM-024

Step 1: Preparation of 2-Chloro-N-ethylacetamide (1)

1

Cl
 \
  \
   C=O
   |
   NH
   |
   Et

Using a 4 L erlenmeyer as reaction vessel, chloroacetyl-chloride (106.8 g, 0.946 mol) was added dropwise at 0° C. over 50 min while stirring magnetically, to a solution of ethylamine 2N in THF (946 mL, 1.89 mol) diluted with 1 L of THF. After the addition was completed, stirring was maintained for 3 h at room temperature. Then, the mixture was filtered, concentrated under reduced pressure and made basic with 1N NaOH (150 mL). EtOAc (200 mL) was added, the layers were separated and the aqueous layer was extracted with EtOAc (3 150 mL). The combined organic layers were washed with brine (200 mL), dried (Na₂SO₄) and the solvent evaporated to provide 1 as a yellow oil (92.81 g, 81% yield). 1H NMR (400 MHz, CDCl₃) δ 6.55 (br s, 1H), 4.02 (s, 2H), 3.34 (m, 2H), 1.17 (t, J=7.3 Hz, 3H).

Step 2: Preparation of N-Ethyl-2-(phenylamino)acetamide (2)

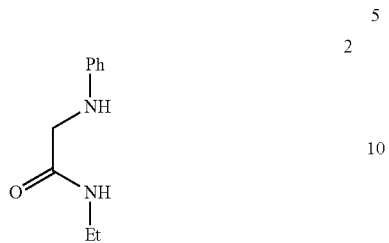

To a solution of 2-chloro-N-ethylacetamide 1 (93.8 g, 0.772 mol) in EtOH (800 mL) was added aniline (216 g, 2.32 mol) in one portion. The reaction was stirred under reflux for 15 h and concentrated. Aqueous NaOH 4N (200 mL) and EtOAc (250 mL) were added. The layers were separated and the aqueous phase was extracted with EtOAc (3×200 mL). The organic layers were combined, washed with brine (400 mL) and dried (Na$_2$SO$_4$). Evaporation of the solvent followed by distillation of the excess aniline under reduced pressure of afforded 2 as a beige solid (126.17 g, 92% yield); mp 51.3°-52.4° C.; 1H NMR (400 MHz, CDCl$_3$) δ 7.20 (t, J=7.4 Hz, 2H), 6.80 (t, J=7.3 Hz, 1H), 6.75 (br s, 1H), 6.61 (dd, J=8.6, 0.9 Hz, 2H), 4.20 (br s, 1H), 3.76 (s, 2H), 3.30 (m, 2H), 1.11 (t, J=7.3 Hz, 3H).

Step 3: Preparation of 3-Chloro-N-(2-(ethylamino)-2-oxoethyl)-N-phenylpropanamide (3)

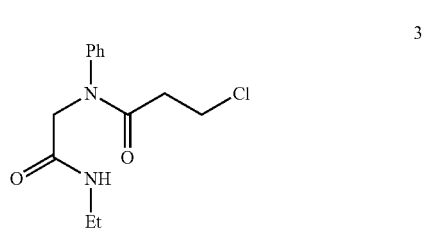 [SMILES: CCNC(=O)CN(C(=O)CCCl)c1ccccc1]

3-Chloropropionylchloride (99.0 g mL, 0.780 mol) was added dropwise over 50 min to a solution of N-ethyl-2-(phenylamino)acetamide 2 (126.2 g, 0.708 mol) in acetone (1 L) at 0° C. The reaction was stirred for 15 h at room temperature, concentrated and poured in 400 mL of water, 400 mL of brine and 200 mL of aqueous NaOH 0.1 M. The mixture was stirred 45 min and filtered. The resulting solid was dried under reduced pressure at 50° C. overnight and yielded 3 as a beige solid (177.8 g, 94% yield). M.p. 133.2-133.8° C.; 1H NMR (400 MHz, CDCl$_3$) δ 7.45-7.37 (m, 3H), 7.28 (m, 2H), 6.41 (br s, 1H), 4.30 (s, 2H), 3.78 (t, J=6.5 Hz, 2H), 3.31 (m, 2H), 2.61 (t, J=6.4 Hz, 2H), 1.15 (t, J=7.3 Hz, 3H).

Step 4: Preparation of N-(3-Chloropropyl)-N-(2-(ethylamino)ethyl)benzenamine (4)

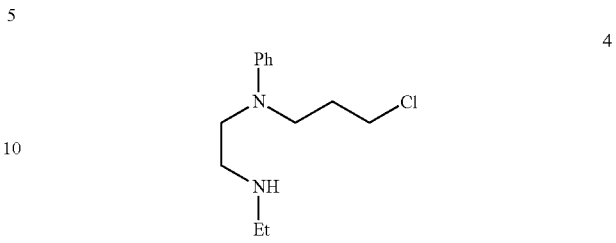

To a solution of 3-chloro-N-(2-(ethylamino)-2-oxoethyl)-N-phenylpropanamide 3 (89.10 g, 0.332 mol) in THF (350 mL) was added BH3·THF 1 N (884 mL, 884 mol) dropwise over 1 h at 0° C. The reaction was stirred 15 h under reflux and quenched by adding MeOH (54 mL, 1.33 mmol) dropwise at room temperature. After stirring for 15 min at room temperature, HCl 4N (221 mL, 0.884 mol) was added and the mixture was heated to reflux until complete hydrolysis of borane material (monitored by HPLC, approximately 2h30 required). The mixture was concentrated under reduced pressure and then poured in a mixture of 200 mL of water, 200 mL of brine and ice. KOH 4N was added until pH 7-8 was obtained. The mixture was extracted with 300 mL of EtOAc (4×). The organic phases were combined, washed with brine (400 mL) and dried (Na2SO4). Evaporation of the solvent to dryness followed by trituration of the resulting solid with pentane/hexane (1:1) yielded 4 as a white solid (57.21 g, 72% yield). 1H NMR (400 MHz, CDCl$_3$) δ 9.50 (br s, 1H), 7.26 (t, J=7.3 Hz, 2H), 6.89 (d, J=8.0 Hz, 2H), 6.78 (t, J=7.3 Hz, 1H), 3.92 (t, J=7.4 Hz, 2H), 3.53 (m, 4H), 3.08 (m, 4H), 2.02 (quint, J=6.2 Hz, 2H), 1.46 (t, J=7.3 Hz, 3H).

Step 5: Preparation of 1-Ethyl-4-phenylhomopiperazine (5)

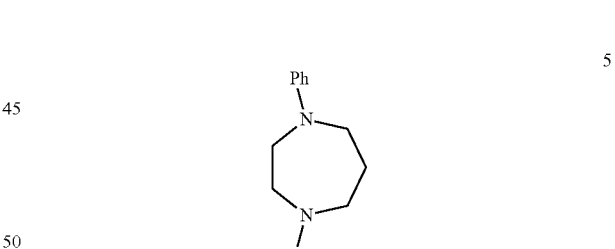

A solution containing N-(3-Chloropropyl)-N-(2-(ethylamino)ethyl)benzenamine 4 (56.83 g, 0.236 mol), KBr (28.09 g, 0.236 mol) and Na$_2$CO$_3$ (25.01 g, 0.236 mol) in DMF (315 mL) was stirred at reflux temperature for 3 h. After cooling and evaporation of the solvent under reduced pressure, the mixture was diluted with NaOH 0.1N (300 mL) and brine (300 mL) and it was extracted with EtOAc (3×300 mL). The organic layers were combined, washed with brine (400 mL), dried (Na$_2$SO$_4$), the solvent was evaporated to an oil which was diluted with 200 mL Et$_2$O. After filtration and evaporation of the solvent, crude 5 was obtained as a brown oil that was distilled under reduced pressure (bp 115°-125° C. under 0.55 mmHg) to provide 5 as a colorless oil (36.35 g, 88% yield). 1H NMR (400 MHz, CDCl$_3$) δ 7.25 (dt, J=2.1, 7.2 Hz, 2H), 6.72 (m, 3H), 3.61 (m, 2H), 3.53 (t, J=6.3

Hz, 2H), 2.80 (m, 2H), 2.62 (m, 4H), 2.03 (m, 2H), 1.12 (t, J=7.1 Hz, 3H); 13C NMR (100 MHz, CDCl₃) δ 149.1, 129.1, 115.6, 111.4, 54.9, 54.0, 51.5, 48.7, 47.8, 27.7, 12.3.

To remove impurity 7, which was formed during the reduction of 3. Crude 5 contaminated with 7 (80.58 g, 0.395 mol) was dissolved in DCM (300 mL) and treated with acetylchloride (18.50 g, 0.237 mol) for 1 h at room temperature. The reaction mixture was extracted 2N HCl (3×200 mL). The combined aqueous layers were made basic with 4N NaOH until pH 8, then they were extracted with EtOAc (6×200 mL). The combined organic layers were dried (Na₂SO₄) and the solvent evaporated. The oily material thus obtained was diluted with Et₂O or MTBE (250 mL), filtration and evaporation gave 5 as a yellow oil (76.71 g, 100% homogeneity by HPLC).

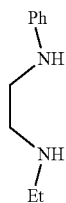

7

Step 6: Preparation of ASM-024

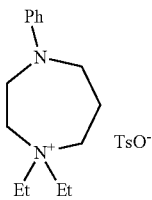

A 5 L three-necked flask, equipped with a mechanical stirrer and a condenser, is charged with 189.55 g (0.93 mol) of 1-phenyl-4-ethyl-homopiperazine and then 1 L of acetone. Ethyl p-toluenesulfonate (371.6 g, 1.86 mol, 2 equiv) plus 200 mL of acetone for wash then added and the mixture was heated gently to reflux temperature. After 4 h, crystals had started to form and 350 ml of acetone were added to facilitate the stirring. After 24 h, HPLC analysis indicated that there was some starting material left. Consequently, 1 additional equivalent of TsOEt was added (186 g) and the mixture was further heated to reflux. After a total of 94 h, HPLC analysis indicated that the reaction had not progress much further and therefore, the heating was stopped and after 1 h, t-butyl methyl ether (1 L) was added. The mixture was stirred 15 min, then the crystals were filtered and washed with 5 portions of 500 mL of t-butyl methyl ether. The fine white needles were dried at room temperature under vacuum for 24 hours to afford 336.86 g (90% yield) of ASM-024: mp 167.5°-168.8° C.; LC-UV-MS analysis: 100% homogeneity (RT=13.4 min) using UV detection at 240 nm and CN column with ACN-H₂O (0.1% formic acid) as gradient eluent; ES(+) m/z 233.2 (M TsO—); ES(-) m/z 171 (TsO—). 1H NMR (D₂O) δ 7.74 (d, 2H), 7.40 (m, 4H), 6.93 (m, 3H), 3.75 (br s, 2H), 3.54 (m, 4H), 3.37 (m, 6H), 2.42 (s, 3H), 2.23 (br s, 2H), 1.32 (t, 6H); 13C NMR (D₂O) δ 6.7, 20.3, 21.5, 42.6, 46.2, 54.5, 59.5, 60.3, 112.8, 117.6, 125.2, 129.0, 129.4, 140.4, 141.2, 147.9.

The crude product ASM-024 (222.11 g) was dissolved in hot CH₂Cl₂ (750 mL). Then, tBuOMe (160 mL) was added slowly in order to create a mild milky vein and until the appearance of the first crystal, and the mixture was left at room temperature for 3 h. Then, the white solid was filtered, washed with tBuOMe (500 mL) and dried under vacuum. For the second and third recrystallization, the same procedure was used with CH₂Cl₂ (750 mL)/tBuOMe (110 mL) and CH₂Cl₂ (720 mL)/tBuOMe (120 mL) respectively, to afford 211.8 g of ASM-024 (99% recovery): LCMS analysis for EtOTs indicated 0.99 ppm.

Example 2 Characterization of ASM-024 from Example 1 i) Simultaneous Thermal Analysis (STA) Testing

Using a Perkin-Elmer TGA2000, approximately 20 mg of ASM-024 was loaded into a tared ceramic crucible, and the sample was heated to 300° C. at a rate of 10° C./minute. A 20 cc/min purge flow of nitrogen was used to prevent any oxidative side reactions. Sample weight and heat flow response was monitored and recorded. A sharp endotherm was seen at onset 164° C. This was assigned as a melt. No other thermal events or weight losses were observed. This indicated that ASM-024 as tested is in the anhydrous crystalline form.

ii) Differential Scanning Calorimetry (DSC) Testing

DSC testing was performed using a Perkin Elmer Jade DSC. Approximately 2 mg of ASM-024 was loaded into an aluminium sample pan and non-hermetically sealed. The sample was heated to 300° C. at a rate of 10° C./minute, and heat flow response was monitored and recorded. The DSC thermogram supports the STA result above, only showing a melt at onset 166° C.

iii) XRPD

XRPD testing was performed using a PANalytical X'pert PRO XRPD. Approximately 20 mg of sample was placed onto a low background XRPD sample holder. The sample was then loaded into the instrument and diffraction patterns recorded using the following experimental conditions:

Tube anode: Cu
Generator tension: 40 kV
Generator current: 40 mA
Wavelength alpha1: 1.5406 Å
Wavelength alpha2: 1.5444 Å
Start angle [2 theta]: 5
End angle [2 theta]: 50
Scan time: 11 minutes FIG. 1 shows a typical diffractogram of dry ASM-024 obtained from example 1. The API was seen to be crystalline with sharp peaks. The crystalline form is designated anhydrous Form I for the purpose of the description herein. Table 1 summarizes the list of peaks of the crystalline ASM-024.

TABLE 1

| No. | Pos. [°2Th.] | FWHM [°2Th.] | Area [cts*°2Th.] | d-spacing [Å] | Height [cts] | Rel. Int. [%] |
|---|---|---|---|---|---|---|
| 1 | 8.2026 | 0.1004 | 77.31 | 10.77926 | 780.89 | 28.07 |
| 2 | 8.9818 | 0.1338 | 237.85 | 9.84585 | 1801.74 | 86.35 |
| 3 | 9.1732 | 0.1004 | 138.61 | 9.64079 | 1400.02 | 50.32 |
| 4 | 10.4746 | 0.2007 | 44.92 | 8.44576 | 226.86 | 16.31 |
| 5 | 13.8222 | 0.8029 | 53.21 | 6.4069 | 67.17 | 19.32 |
| 6 | 15.278 | 0.1338 | 48.97 | 5.79951 | 370.98 | 17.78 |
| 7 | 16.1464 | 0.1004 | 72.08 | 5.48953 | 727.97 | 26.17 |

TABLE 1-continued

| No. | Pos. [°2Th.] | FWHM [°2Th.] | Area [cts*°2Th.] | d-spacing [Å] | Height [cts] | Rel. Int. [%] |
|---|---|---|---|---|---|---|
| 8 | 16.3634 | 0.1004 | 115.82 | 5.41721 | 1169.84 | 42.05 |
| 9 | 17.5626 | 0.1004 | 112.25 | 5.04991 | 1133.72 | 40.75 |
| 10 | 18.0752 | 0.1673 | 135.5 | 4.90786 | 821.12 | 49.19 |
| 11 | 18.2573 | 0.1004 | 76.73 | 4.85931 | 774.99 | 27.86 |
| 12 | 18.856 | 0.1004 | 197.76 | 4.70633 | 1997.46 | 71.79 |
| 13 | 19.0333 | 0.1004 | 169.69 | 4.66291 | 1713.94 | 61.6 |
| 14 | 19.8906 | 0.1004 | 32.74 | 4.46382 | 330.66 | 11.88 |
| 15 | 20.2545 | 0.1004 | 54.62 | 4.38443 | 551.7 | 19.83 |
| 16 | 20.5537 | 0.2676 | 275.46 | 4.32128 | 1043.32 | 100 |
| 17 | 20.9122 | 0.1004 | 137.27 | 4.24801 | 1386.45 | 49.83 |
| 18 | 21.339 | 0.1004 | 23.85 | 4.164 | 240.84 | 8.66 |
| 19 | 21.736 | 0.3346 | 104.72 | 4.08883 | 317.3 | 38.02 |
| 20 | 22.4503 | 0.1004 | 97.67 | 3.96033 | 986.52 | 35.46 |
| 21 | 22.6217 | 0.1004 | 141.6 | 3.9307 | 1430.14 | 51.4 |
| 22 | 23.8494 | 0.1338 | 45.08 | 3.73107 | 341.52 | 16.37 |
| 23 | 25.0483 | 0.1004 | 97.66 | 3.55515 | 986.41 | 35.45 |
| 24 | 26.222 | 0.1338 | 71.01 | 3.39861 | 537.89 | 25.78 |
| 25 | 26.431 | 0.1338 | 99.6 | 3.37221 | 754.52 | 36.16 |
| 26 | 27.7048 | 0.1004 | 54.36 | 3.22 | 549.09 | 19.74 |
| 27 | 27.9132 | 0.1338 | 102.7 | 3.19644 | 777.97 | 37.28 |
| 28 | 29.0577 | 0.1171 | 63.85 | 3.07308 | 552.8 | 23.18 |
| 29 | 29.428 | 0.1004 | 46.71 | 3.03525 | 471.74 | 16.96 |
| 30 | 30.1912 | 0.2007 | 39.53 | 2.96024 | 199.64 | 14.35 |
| 31 | 30.7341 | 0.1673 | 39.17 | 2.90917 | 237.35 | 14.22 |
| 32 | 32.7089 | 0.3346 | 65.76 | 2.73791 | 199.26 | 23.87 |
| 33 | 34.9665 | 0.2676 | 46.97 | 2.56614 | 177.92 | 17.05 |
| 34 | 35.6949 | 0.1338 | 35.1 | 2.51543 | 265.9 | 12.74 |
| 35 | 36.1958 | 0.1338 | 35.26 | 2.48176 | 267.11 | 12.8 |
| 36 | 37.2009 | 0.2007 | 43.95 | 2.41698 | 221.95 | 15.96 |
| 37 | 37.867 | 0.1004 | 24.62 | 2.37599 | 248.69 | 8.94 |
| 38 | 39.4215 | 0.1673 | 42.44 | 2.2858 | 257.2 | 15.41 |
| 39 | 40.0555 | 0.1004 | 47.77 | 2.25107 | 482.49 | 17.34 |
| 40 | 40.6543 | 0.2007 | 47.58 | 2.21929 | 240.27 | 17.27 |
| 41 | 41.1541 | 0.2007 | 54.42 | 2.19349 | 274.85 | 19.76 |
| 42 | 42.3166 | 0.3346 | 69.33 | 2.13588 | 210.06 | 25.17 |
| 43 | 43.3031 | 0.1338 | 44.75 | 2.08948 | 338.96 | 16.24 |
| 44 | 44.7201 | 0.2007 | 40.93 | 2.02651 | 206.71 | 14.86 |
| 45 | 48.4688 | 0.3264 | 70.01 | 1.87662 | 160.88 | 25.42 |

In one embodiment, Form I is defined by one or more peaks defined in table 1. In particular, Form I may be defined by one or more characteristic peaks.

The XRD pattern of ASM-024 Form I is characterized by 16 peaks. Table 2 represents the positions of these peaks according to the solid state form.

TABLE 2

| | Form I | |
|---|---|---|
| Peak # | 2θ | d spacing (Å) |
| 1 | 8.2 | 10.770 |
| 2 | 9.2 | 9.647 |
| 3 | 10.4 | 8.494 |
| 4 | 15.3 | 5.783 |
| 5 | 16.3 | 5.433 |
| 6 | 17.7 | 5.006 |
| 7 | 18.2 | 4.876 |
| 8 | 18.8 | 4.722 |
| 9 | 20.4 | 4.353 |
| 10 | 20.8 | 4.272 |
| 11 | 21.8 | 4.073 |
| 12 | 22.5 | 3.945 |
| 13 | 23.7 | 3.743 |
| 14 | 25.0 | 3.557 |
| 15 | 26.3 | 3.382 |
| 16 | 27.8 | 3.207 |

The XRP pattern of ASM-024 Form I could be further characterised and classified by the intensity of the peaks relative to each other. Two % of peaks relative intensity patterns were determined according the highest value of the peak #7 or 8 (Table 3 and 4).

TABLE 3

% of Peaks Intensity Relative to Peak #7 of ASM-024 FORM I.

| Peak # | d-spacing (Å) | Position (2θ) | % of Intensity relative to peak #7 | | | | |
|---|---|---|---|---|---|---|---|
| | | | Ave. | σ | RSD(%) | Min. | Max. |
| 1 | 88.271 | 8.203 | 11.7 | 1.6 | 13.6 | 10.4 | 14.4 |
| 2 | 44.137 | 9.159 | 55.2 | 19.9 | 36.1 | 34.1 | 82.9 |
| 3 | 29.427 | 10.407 | 7.9 | 1.8 | 22.5 | 6.2 | 11.1 |
| 4 | 22.072 | 15.310 | 3.6 | 2.1 | 58.8 | 0.0 | 5.8 |
| 5 | 17.660 | 16.301 | 40.2 | 12.1 | 30.2 | 25.9 | 60.0 |
| 6 | 14.718 | 17.702 | 20.3 | 6.8 | 33.2 | 14.6 | 30.6 |
| 7 | 12.618 | 18.180 | 100.0 | 0.0 | 0.0 | 100.0 | 100.0 |
| 8 | 11.043 | 18.778 | 18.5 | 11.8 | 63.5 | 7.5 | 35.9 |
| 9 | 9.818 | 20.384 | 8.8 | 4.7 | 53.5 | 3.2 | 13.7 |
| 10 | 8.838 | 20.777 | 44.5 | 21.9 | 49.3 | 24.4 | 81.9 |
| 11 | 8.037 | 21.802 | 8.7 | 3.2 | 36.7 | 5.2 | 13.7 |
| 12 | 7.369 | 22.519 | 17.8 | 7.6 | 42.7 | 8.2 | 27.2 |
| 13 | 6.805 | 23.750 | 7.2 | 3.5 | 48.3 | 3.5 | 12.8 |
| 14 | 6.321 | 25.014 | 9.2 | 2.5 | 27.5 | 6.4 | 12.4 |
| 15 | 5.901 | 26.329 | 16.9 | 3.0 | 17.9 | 13.4 | 21.6 |
| 16 | 5.535 | 27.799 | 13.4 | 1.6 | 11.8 | 11.4 | 15.3 |

TABLE 4

% of Peaks Intensity Relative to Peak #8 of ASM-024 FORM I

| Peak # | d-spacing (Å) | Position (2θ) | % of Intensity relative to peak #8 | | | | |
|---|---|---|---|---|---|---|---|
| | | | Ave. | σ | RSD(%) | Min. | Max. |
| 1 | 88.271 | 8.203 | 27.8 | 13.9 | 49.9 | 15.6 | 49.7 |
| 2 | 44.137 | 9.159 | 57.4 | 24.4 | 42.6 | 33.8 | 95.8 |
| 3 | 29.427 | 10.407 | 13.3 | 4.5 | 33.9 | 9.9 | 21.7 |
| 4 | 22.072 | 15.310 | 15.5 | 4.0 | 25.6 | 10.9 | 21.7 |
| 5 | 17.660 | 16.301 | 73.5 | 23.7 | 32.3 | 52.6 | 113.3 |
| 6 | 14.718 | 17.702 | 33.4 | 17.5 | 52.4 | 15.2 | 56.8 |
| 7 | 12.618 | 18.180 | 54.9 | 26.8 | 48.8 | 33.8 | 98.6 |
| 8 | 11.043 | 18.778 | 100.0 | 0.0 | 0.0 | 100.0 | 100.0 |
| 9 | 9.818 | 20.384 | 43.1 | 5.1 | 11.9 | 39.8 | 52.2 |
| 10 | 8.838 | 20.777 | 81.0 | 29.7 | 36.7 | 56.0 | 121.0 |
| 11 | 8.037 | 21.802 | 17.2 | 5.3 | 30.7 | 10.5 | 24.4 |
| 12 | 7.369 | 22.519 | 70.9 | 13.6 | 19.2 | 45.5 | 82.8 |
| 13 | 6.805 | 23.750 | 14.3 | 4.5 | 31.2 | 9.7 | 21.0 |
| 14 | 6.321 | 25.014 | 31.9 | 9.6 | 30.1 | 21.8 | 49.4 |
| 15 | 5.901 | 26.329 | 29.4 | 9.4 | 32.1 | 17.8 | 42.7 |
| 16 | 5.535 | 27.799 | 38.9 | 14.4 | 37.1 | 27.1 | 65.5 |

Example 3 Particle Size Reduction by Air Jet Milling

A 2 g sample of anhydrous crystalline ASM-024 was taken and fed through the Sturtevant Qualification Micronizer. The mill has a 2 inch chamber, and was operated at 80 psig grinding pressure and 90 psig feed pressure. Milled API was recovered from the exhaust filter sock and physically characterized.

PSD

Particle size analysis was performed using a Malvern Mastersizer with a Small Sample Presentation Unit. The dispersant used was ethyl acetate with 2 g of SPAN 85 per liter. Samples were prepared by sonicating 5 mg of sample in 2 ml of dispersant, the sample was then added dropwise to achieve 20% obscuration.

Figure 2:
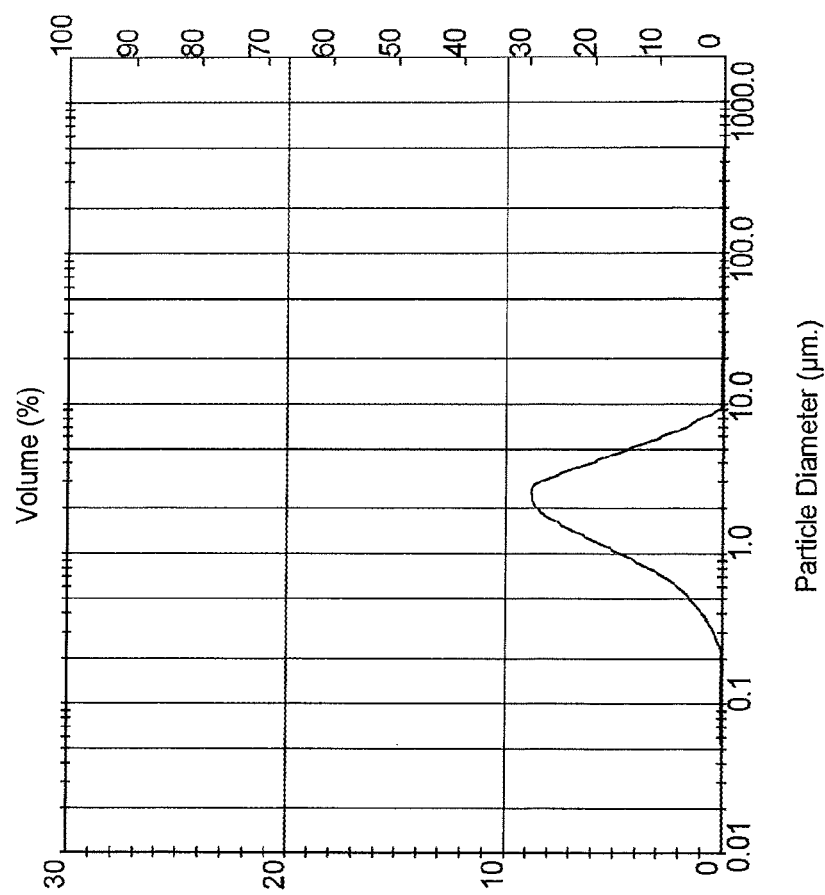

Table 5 summarizes the PSD distribution obtained for ASM-024 prior to and after micronization which shows a typical size range for unmicronized material. FIG. 2 shows the particle size distribution of milled API after one pass through the air jet mill. The particle size range has been significantly reduced. This suggests that one pass milling produces a fine powder having a size suitable for inhalation.

TABLE 5

|  | $d_{10}$ | $d_{50}$ | $d_{90}$ |
|---|---|---|---|
| Size (μm) Example of PSD of ASM-024 prior to micronization | 13.92 | 41.67 | 91.89 |
| PSD of ASM-024 after one pass in Jet air mill. | 0.78 | 2.10 | 4.70 |

Figure 4:
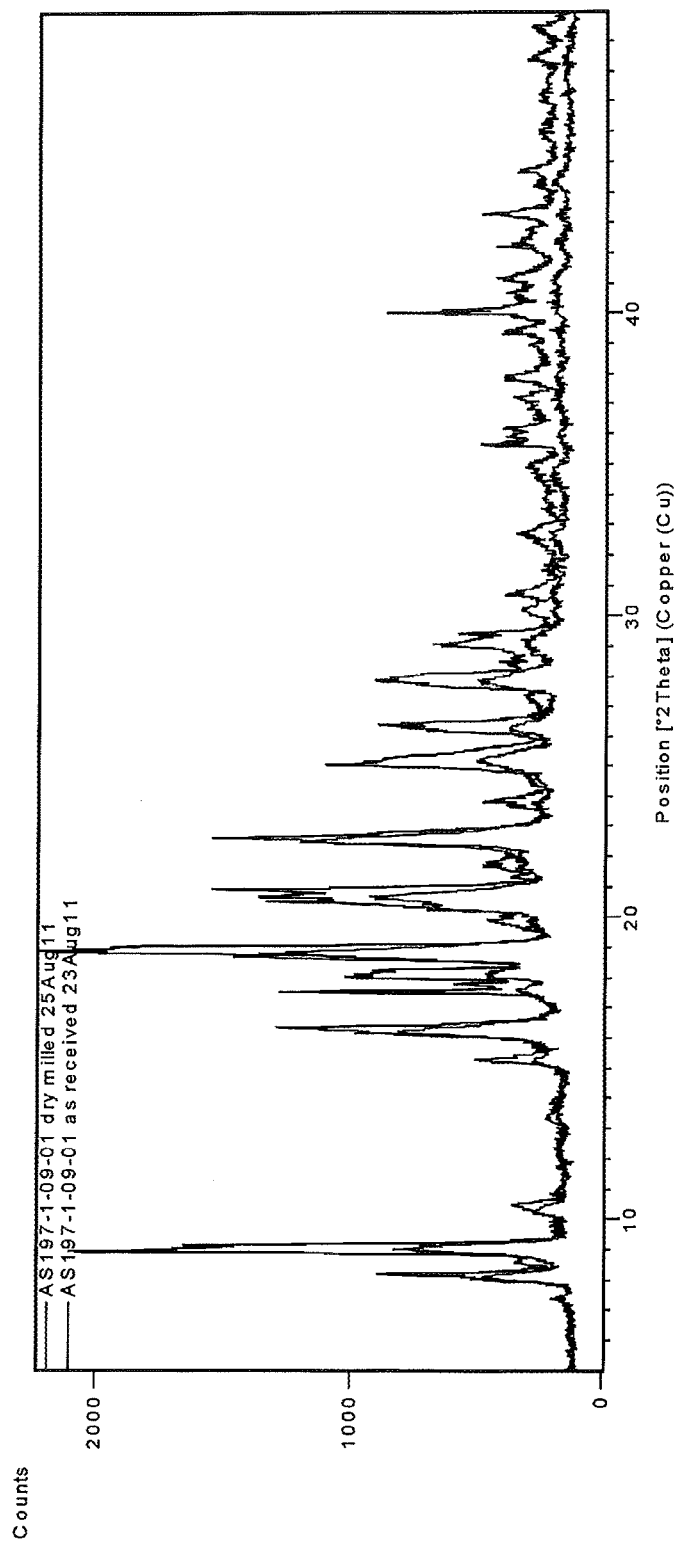

FIG. 4 shows the XRPD diffractogram of milled ASM-024 overlaid with the diffractogram of unmilled ASM-024. No significant change is seen in the XRPD diffractogram after milling. There has been a reduction in peak intensity due to the reduced particle size so some minor peaks are no longer observed, but all the major peaks align correctly. This showed that the polymorphic form of the API is not changing during milling.

Example 4 In Vitro Method for Assessment of Properties of Micronized ASM-024

In vitro testing of the active agent allows for assessing whether a correct and reproducible amount of the agent will likely be deposed in the lung upon inhalation. One instrument for measuring the aerodynamic particle size of inhalers is the Cascade Impactor (CI). Cascade impaction essentially provides a size classification of particles in an air stream. Next Generation Impactors (NGIs) are known in the art and are used for evaluation of inhaled products.

For method development using the NGI method, size three HPMC capsules were hand filled with forty milligrams of micronized ASM-024. Three capsules were tested according to manufacturer's instructions using the following conditions:
Cup coating agent: 3% PEG400 with 0.1% F68 in acetone
Testing flow rate: 60 LPM
Testing volume: 4 L (4 second actuation)
Device: Miat Monodose Inhaler (standard resistance)
Sample diluent: 70% MeOH: 30% $H_2O$ (v/v)
Dilutions
 Device—50 ml
 Throat—50 ml
 Pre-separator—100 ml
 Stage 1—MOC—10 ml
 Filter—50 ml
An analysis of the results showed that for the NGI method a good recovery is seen from all three replicates and good reproducibility is seen between all three replicates. This method was considered suitable for analysis of ASM-024.

Example 5 Assessment of Active Ingredient Properties, DPI and Capsule Shell i) Co-Milling with Magnesium Stearate The addition of magnesium stearate to inhalation powders is reported to improve aerosol performance and increase moisture resistance. ASM-024 was co-milled with magnesium stearate at 0.2%, 0.5%, 1.0%, 2.0% w/w.

Magnesium stearate was blended with un-milled ASM-024 in two gram lots. Approximately one gram of ASM-024 was weighed into a 28 ml vial. The appropriate mass of magnesium stearate was then weighed on top of the API and the weight completed to two grams with ASM-024. The materials were blended using a Turbula T2F mixer at 101 rpm for ten minutes. The blended material was passed through the Sturtevant Qualification Micronizer and recovered from the filter sock.

Table 6 shows the PSDs of the milled materials. No significant effect on PSD was seen when milling with increasing concentrations of magnesium stearate. XRPD diffractograms of the neat and magnesium stearate-ASM-024 blended together showed no new or changing peaks after milling with magnesium stearate. The DSC thermogram of ASM-024 milled with 2% w/w magnesium stearate similarly showed no new thermal events. Also, an overlay of XRPD diffractograms of the ASM-024 alone or blended with magnesium stearate showed no new or changing peaks after milling with magnesium stearate.

TABLE 6

| % Magnesium Stearate | $d_{10}$ | $d_{50}$ | $d_{90}$ |
|---|---|---|---|
| 0.0 | 0.97 | 1.95 | 3.80 |
| 0.2 | 0.89 | 1.74 | 3.33 |
| 0.5 | 0.89 | 1.86 | 3.94 |
| 1.0 | 0.90 | 1.70 | 3.17 |
| 2.0 | 0.91 | 1.69 | 3.11 | ii) Aerosol testing—Device and Capsule Shell Comparative Testing

Figure 3:
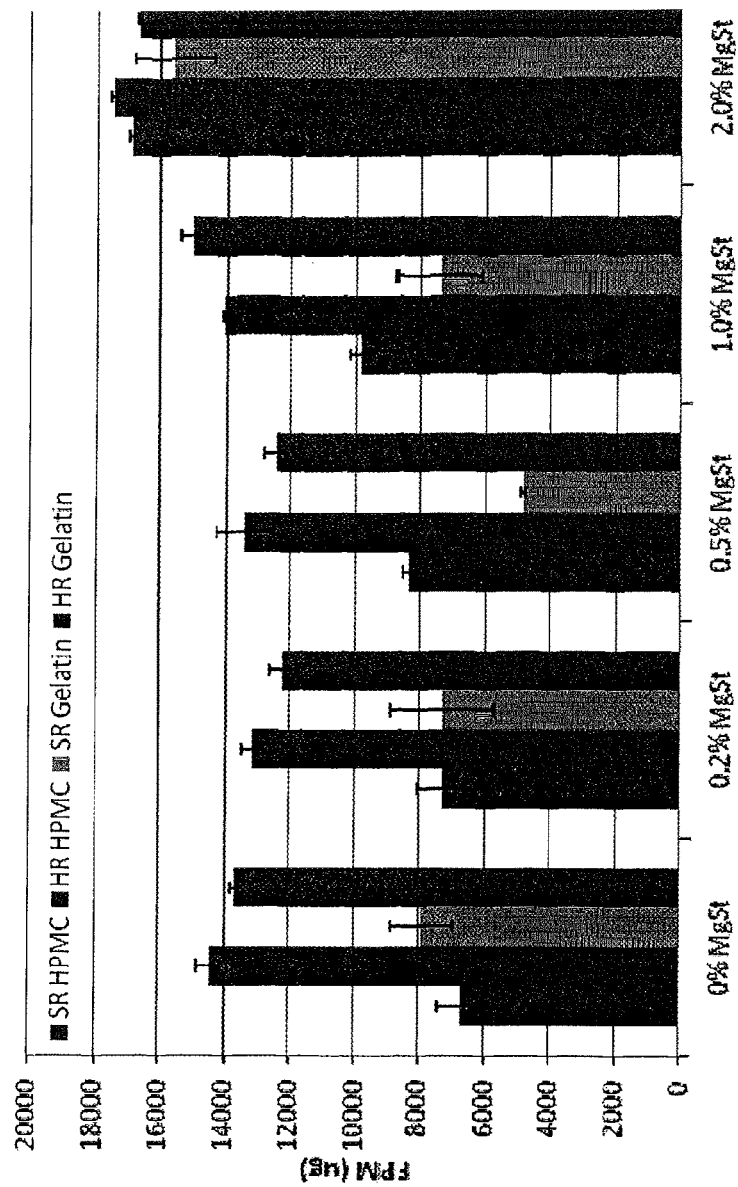

Aerosol performance and stability was assessed. Milled API was hand filled into size 3 HPMC capsules and size 3 gelatin capsules (40 mg capsule fill weight). NGI testing was performed in duplicate using standard resistance and high resistance Miat Monodose inhalers. FIG. 3 shows the fine particles mass (FPM) results of NGI testing. It was possible to demonstrate that a suitable FPM can be obtained with the inhaler. The high resistance device has provided an increased FPM of ASM-024 from both HPMC and gelatin capsules. The high resistance device provided in this assay showed a lower % RSDs than the standard resistance device results. Gelatin capsules showed higher % RSDs of FPM compared to HPMC capsules and showed a lower average FPM either in standard or high resistance devices.

The mass of ASM-024 retained in the device and capsule after NGI testing showed that the high resistance device retained greater quantities of ASM-024 than the standard resistance device, however an acceptable level of retained substance was achieved and generally less than about 20 mg was retained in the device and capsule.

Good aerosol performance (i.e. under NGI testing condition) was also seen from HPMC capsules with low fill weights at 1.7 mg, 4.3 mg and 8.7 mg and 34.7 mg micronized ASM-024 conducted in triplicate for each fill weight.

iii) ASM-024 Capsule Stability Study

A two month study was performed at accelerated conditions with testing at two weeks, four weeks and eight weeks. Hand filled 40 mg capsules were packed in foil pouches with a 10 g desiccant pouch and heat sealed. Hand filled 40 mg capsules were also packed in foil pouches and heat sealed without a desiccant pouch. All heat seals were hand checked to ensure seal integrity. Pouches were placed on stability at 40° C./75% RH. NGI testing of the capsules stored without desiccant were conducted over the eight week study. A steady decrease in FPM is seen over the study period, however only 10.9% decrease was observed after a total of eight weeks at 40° C./75% RH for the capsules without desiccant. The results of NGI testing of capsules stored with desiccant over the eight week study showed a decrease of about only 5.7%.

iv) High Speed Filling

Harro Höfliger™ Modu-C high speed filling machine with a drum dosing unit designed for filling capsules with formulations for inhalation. Suitable conditions for filling micronized ASM-024 into capsules could be identified for providing consistent dosing.

ASM-024 was air jet milled and passed through a 250 um sieve and capsules were filled with a single or multiple doses (up to 8 doses). The experiments showed that fill weight scales in a linear fashion with increasing doses from about 5 to about 40 mg ASM-024 and that suitable fill weight was achieved with an acceptable % RSD A similar study was also performed to scope filling performance of ASM-024 milled with 2% w/w magnesium stearate. 125 g of API was milled with 2% w/w magnesium stearate and passed through a 250 um sieve. Capsules were filled with one dose of milled and sieved API and collected for analysis. The assay results showed that the mean fill weight is higher than ASM-024 without magnesium stearate. The % RSD in the tested capsules was higher than the % RSD ASM-024 without magnesium stearate but still within acceptable limits. The filling experiment was scaled up to achieve a 40 mg capsule fill weight using 3 to 7 shots and the results showed that the desired fill was obtained with an acceptable % RSD.

Machine filling was also suitably effected at varying ranges of micronized ASM-024 content in capsules using another equipment type known as Xceledose™.

The invention claimed is:

1. A compound having the formula Ia:

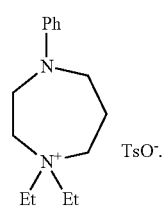

2. The compound of claim 1 in a crystalline form.

3. The compound of claim 2, wherein said crystalline form is form I.

4. The compound of claim 1 in a micronized crystalline form.

5. The compound of claim 4 wherein said micronized crystalline form is form I.

6. The compound of claim 4 wherein said micronized crystalline form has a particle size less than about 10 microns.

7. The compound of claim 4, wherein said micronized crystalline form has a particle size of between about 1 microns to 5 microns.

8. A process for preparing a compound of formula Ia

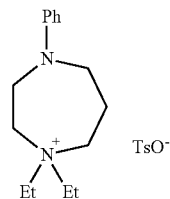

comprising the steps of cyclizing a compound of formula 4a

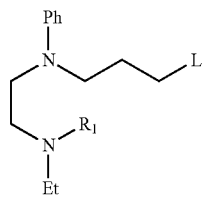

wherein $R_1$ is H and L is a leaving group; to provide a compound of formula 5

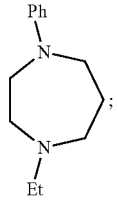

and reacting said compound 5 with ethyl p-toluenesulfonate for introducing an ethyl group on the non-aromatic tertiary amine and produce said compound of formula Ia.

9. The process of claim 8, wherein said compound of formula 4a is prepared by:

reacting an ethylamine of formula EtNH-$R_1$ with a reagent of formula LCH$_2$(CO)L, wherein $R_1$ is H and L are the same or different and are a leaving group to provide the amide 1a

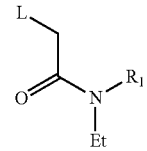

wherein $R_1$ and L are the same as defined above;

reacting said compound 1a with aniline to provide compound 2a

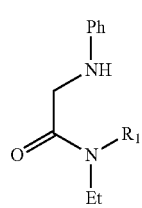
2a
wherein R1 is the same as defined above;
reacting compound 2a with a reagent of formula LCH$_2$CH$_2$(CO)L wherein L are as defined previously, to provide compound of formula 3a
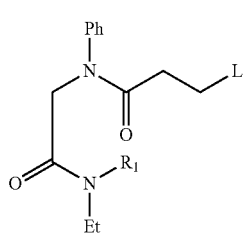
3a
wherein L is as defined previously, and reducing said compound 3a with a reducing agent to provide compound 4a.
* * * * *